United States Patent [19]
Whiteford

[11] Patent Number: 5,562,705
[45] Date of Patent: Oct. 8, 1996

[54] SUTURELESS WOUND CLOSURE DEVICE

[76] Inventor: Carlton L. Whiteford, 3 High Point Rd., Westport, Conn. 06880

[21] Appl. No.: 447,626

[22] Filed: May 23, 1995

[51] Int. Cl.$^6$ ................................................ A61B 17/00
[52] U.S. Cl. ........................ 606/215; 606/213; 606/216
[58] Field of Search ................................. 606/213, 215, 606/216, 212, 116, 150, 221, 1

[56] References Cited

U.S. PATENT DOCUMENTS

| | | | |
|---|---|---|---|
| 363,538 | 5/1887 | Penny | 606/216 |
| 2,223,006 | 11/1940 | Laub | 606/216 |
| 3,983,878 | 10/1976 | Kawchitch | 606/216 |
| 4,539,990 | 9/1985 | Stivala | 606/215 |
| 4,702,251 | 10/1987 | Sheehan | 606/216 |
| 5,122,147 | 6/1992 | Sewell, Jr. | 606/116 |
| 5,192,270 | 3/1993 | Carswell, Jr. | 606/116 |

*Primary Examiner*—Michael Powell Buiz
*Assistant Examiner*—Jeffrey A. Schmidt
*Attorney, Agent, or Firm*—Spencer E. Olson

[57] ABSTRACT

A method for opening and closing an incision in which a plurality of opposed sets of aligned closure components are adhesively adhered to a patient's skin, prior to making the incision, along opposite sides of the intended incision and spaced a first distance from one another transversely of the incision line. After the surgeon has made the incision and closed the wound in conventional fashion except for final closing of the epidermis, a bridge having a length shorter than the first distance anchored between the opposed closure components and spanning the incision draws the closure components toward each other so as to bring the skin at the edges of the wound into alignment and everting contact under a slight, but precise amount of tension which is maintained while the wound heals. The closure components and the bridge are all perforated and thus breathable, and the bridge material is transparent so as to permit healing of the incision to be monitored.

20 Claims, 2 Drawing Sheets

SUTURELESS WOUND CLOSURE DEVICE

BACKGROUND OF THE INVENTION

This invention relates generally to surgical methods and apparatus and, more particularly, to apparatus for effecting closure of surgical incisions without using sutures, staples or other invasive devices.

In known sutureless surgical techniques, upon conclusion of the surgical procedure the opposed skin edges of the incision are re-approximated and then held in position by tape, laces, glue and the like, until healing is completed. For example, U.S. Pat. No. 2,752,921 to A. S. Fink entitled "Surgical Dressing for Closing Wounds", describes a wound closing system wherein two strips are adhered to the skin, after the incision is made, at opposite sides of the incision. The strips are drawn toward one another by laces coacting with opposed hooks secured to the strips and thereby close the wound. Being applied after the incision has been made, with no apparent means for aligning, the strips can provide little more than a crude re-approximation of the edges of the wound, which could lead to excessive scarring.

U.S. Pat. No. 4,966,605 to W. R. Thieler entitled "Method for Opening and Closing Surgical Wounds", describes a procedure in which an elastic member is adhered to the patient's body at the site of the intended incision, and the incision made by first cutting through the elastic member and then the patient's skin, and conducting the necessary surgical procedure. Following closure of the wound, the skin at opposite edges of the incision is re-approximated by bringing together the edges of the slitted elastic member and adhering a relatively inelastic sealing member to the elastic member to maintain the edges of the slit in the elastic member (and thus, the skin at the edges of the wound) together in abutting relationship while the wound heals. To accommodate the possibility that more than one attempt will be required to accurately re-approximate the skin at the prepped edges, a pressure-sensitive adhesive is used on the sealing member to enable it to be repeatedly removed and re-positioned.

Improper re-approximation of the skin at the edges of a surgical incision can interfere with healing and may lead to skin irregularities, excessive scarring and keloiding, i.e., formation of fibrous tumors arising from connective tissue of the skin. Among known attempts to match the cut edges of the skin during sutureless closing of an incision is that described in U.S. Pat. No. 4,976,726 to C. E. Haverstock entitled "Skin Closure Devices", wherein markings are applied to opposite sides of the intended incision for use in realigning the cut edges of the incision during closure to assure an abutting relationship. Proper alignment becomes more difficult as the length of the incision increases.

The above described sutureless techniques not only fail to provide accurate and rapid re-approximation of the cut edges of the skin but result, at best, in bringing the skin at opposite sides of the incision into an abutting relationship. However, for improved healing it is considered preferable that the opposed edges of the skin be brought sufficiently close together to cause the joined edges to evert, that is, turn outward slightly, an effect also known as "tenting", as opposed to bringing the edges into abutting relationship. This promotes blood flow through connecting tissue of the opposed edges of the incision resulting in accelerated healing and a thinner scar line because the skin is healed without tension. The described prior art sutureless surgery techniques fail to provide everting contact or "tenting" of the skin at the opposed edges of the incision.

Accordingly, a primary object of the present invention is to provide an improved system for effecting rapid and accurate closure of a surgical incision.

A more specific object of the invention is to provide a system of closure components for aligning and bringing the opposed edges of an incision together in an everted or "tented" relationship, without use of sutures, staples or other invasive devices.

SUMMARY OF THE INVENTION

These and other objects are achieved by a system of closure units employed as follows for effecting closure of a surgical incision:

(1) marking on the patient's skin a line along which the incision is to be made;
(2) adhering to the patient's skin, at opposite sides of the incision line, prior to making the incision, multiple opposed sets of precisely aligned closure units, spaced from each other transversely of the incision line by a first distance;
(3) making an incision along the incision line through the skin and subcutaneous tissue layers, retracting opposed sides of the incision as necessary, and performing the surgical procedure; and
(4) after suturing the subcutaneous tissue layers and closing the incision, establishing bridges between opposed sets of aligned closure units, each bridge having a length shorter than said first distance, which draw the closure components toward one another and bring the edges of the wound into everting contact under a slight, but precise amount of tension.

BRIEF DESCRIPTION OF THE DRAWINGS

Other objects, features and advantages of the invention will become apparent, and its construction and operation better understood, from the following detailed description taken in conjunction with the accompanying drawings, in which.

DETAILED DESCRIPTION OF THE PREFERRED EMBODIMENT

Figure 1:
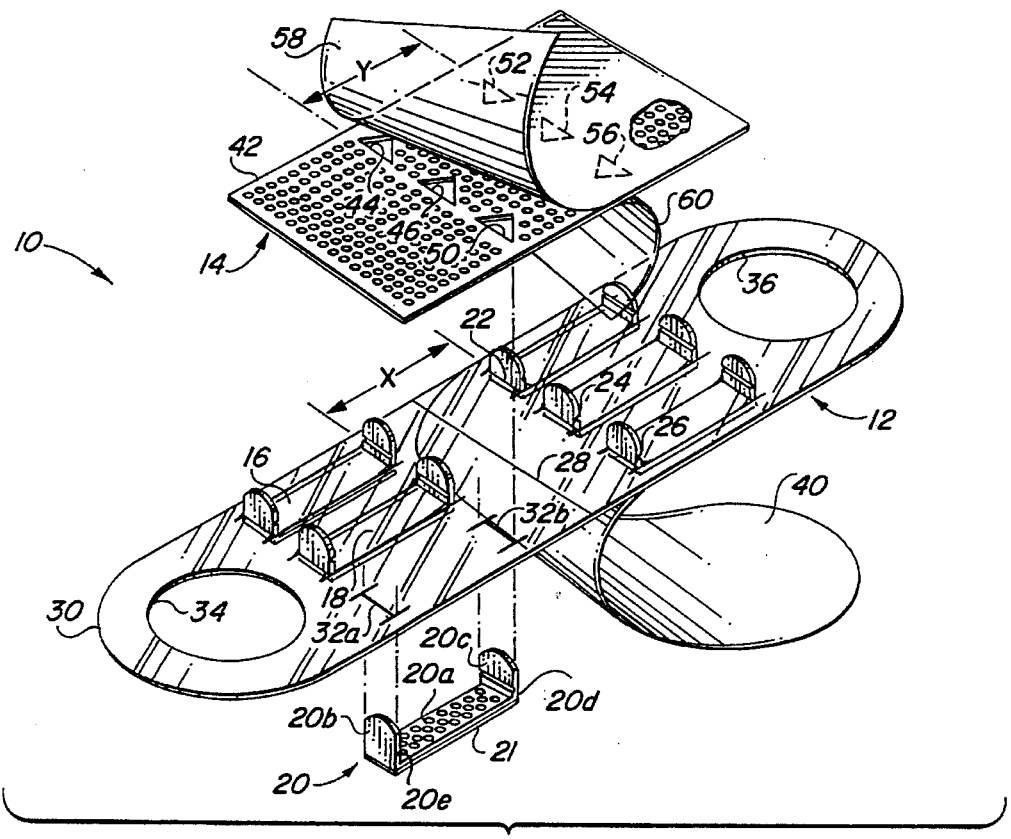
FIG. 1 is a perspective view of a closure unit constructed in accordance with the present invention.

Referring to FIG. 1, the closure unit 10 in accordance with the invention consists of two major parts: a modular closure unit 12 which includes a plurality of closure components, and a cover sheet 14 which coacts with the closure components to bring the edges of an incision into everting contact. Both are packaged in a sterile, peelable envelope (not shown) similar to that used by Johnson & Johnson to package wide "Band-Aid" plastic strips.

Each closure component, one of which 20 is shown removed from the closure unit, is generally rectangular in shape having a bottom wall 20a, typically 16 mm long and 4 mm wide, and integral upstanding tabs 20b and 20c at opposite ends, each typically 2.5 mm long. It is preferably stamped from thin sheet stainless surgical steel, typically 0.5 mm thick. The bottom wall 20a is highly perforated with 0.5 mm diameter holes spaced 0.5 mm apart in both directions, for example, and tabs 20b and 20c preferably are imperforate, that is, devoid of holes for reasons which will become apparent later. The upper ends of tabs 20b and 20c are arcuately rounded to facilitate placement thereover of slots in cover sheet 14 when closing an incision. The tabs may be pre-scored along lines 20d and 20e disposed parallel to and typically ⅟₃₂-inch above bottom wall 20a, so that they can be bent over, if desired, following closure of the incision.

In accordance with an important aspect of the invention, two rows of these components are held in place by a discardable transparent plastic template 30, punched to provide slits 32a and 32b to hold the tabs of the components. For convenience in handling and ease of placement in most surgical situations, template 30 may be two inches long and one inch wide and fabricated from thin transparent sheet plastic, for example, clear polyester sheet having a thickness in the range between about 10 mm and about 15 mm. Preferably, template 30 is fabricated from Mylar, a polyethylene terephalate available from E. I. du Pont de Nemours, Inc., Wilmington, Del., which has been biaxially oriented and heat set to provide dimensional stability and adequate strength. Finger holes 34 and 36 are provided at opposite ends of the template for facilitating handling, and a transverse line 28 is printed thereon at mid-length.

In the illustrated embodiment, template 30 has two opposed sets of slits punched therein, one set being visible at 32a, 32b, which are arranged three to either side of and preferably, but not necessarily, with the innermost ends of the two sets equidistantly spaced from transverse line 28. The slits are I-shaped and dimensioned to receive and frictionally engage the upstanding tabs of respective closure components, and hold the bottom wall 20a against the underside of template 30. The three closure components of each set are precisely aligned with the three components of the other set; specifically, closure components 16, 18 and 20 comprising the set to the left of line 28 are aligned with closure components 22, 24 and 26, respectively, of the set to the right of line 28. The distribution of the slits across the width of template 30 is such that the central pair of slits in each set is equally spaced from the two outer pairs of slits and the outermost slits are spaced from a respective edge of the template by one-half the spacing between slit pairs so that when two or more templates are affixed side-by-side to a patient's skin, the closure components carried thereby will be distributed evenly along the length of the incision. The innermost tabs of the opposed sets of closure components are precisely spaced apart by a distance "X" and, as noted earlier, preferably equidistant from line 28. Typically, the dimension "X" may be 19 mm which, when line 28 is placed over the line on the patient's skin at which the incision is to be made, locates the innermost tabs 9.5 mm to either side of the incision line.

The underside surface of bottom wall 20a of the six closure components are pre-coated with a highly tacky, epidermal-friendly adhesive coating 21 capable of effectively adhering the closure component to the skin of a patient about to undergo surgery. The adhesive is selected to mate with an adhesive previously applied to the patient's skin, a solution of natural rubber in hexane such as that available from Beiersdorf Inc., South Norwalk, Conn., and then dried. The adhesive fills the perforations in bottom wall 20a, which enhances adherence of the closure component to the skin, and is preserved and protected by a discardable peel-away strip 40, which may be siliconized release paper; the plastic template 30 itself is not adhesively coated.

Cover sheet 14, the other element of closure unit 10, is an elongate rectangular plastic sheet 42 of the same width as template 30, namely, one-inch, and is of a length to fit between the outermost tabs of opposed closure components comprising the two sets carried by template 30 which, in the present embodiment is 1¹³⁄₁₆ inches. Cover sheet 14 is fabricated from thin, inelastic, transparent and perforate sheet plastic 42, preferably Mylar, having a thickness in the range between about 10 mm and about 15 mm. Sheet 42 has two opposed sets of aligned slots 44, 46, 50 and 52, 54, 56 formed therein, preferably by punching, each of which is triangular in shape and dimensioned and oriented to receive an upstanding tab of a closure component. The slots of the two sets are distributed across the width of cover sheet 42 with the same spacings as the slits in template 30 and are spaced from one another along the length dimension of sheet 42, by a second distance "Y" slightly shorter than the distance "X" established by template 30 between innermost tabs of the opposed sets of closure components. In the present embodiment, dimension "Y" may be 17 mm, two millimeters less than dimension "X". The preforate plastic strip 42 is coated with a highly tacky epidermal-friendly adhesive similar to or the same as that used on the closure components, which is preserved and protected by peel-away silicone coated paper strips 58 and 60 covering both surfaces of strip 42.

Preparatory to surgery, the area of a patient's body surrounding the planned incision is conventionally prepped by shaving and sterilization, and then coated with a solution such as tincture of benzoine containing an ingredient chemically mated with the adhesive coating on the underside of the bottom walls of the closure components. The surgeon marks the epidermis along the intended length of the incision, typically with a blue line 70, and then selects that number of packages of closure units which, when placed side-by-side along the line, will exceed the length of the planned incision. For example, if the planned length is five inches, the surgeon may call for seven closure units to take care of the possibility that a longer incision may be needed. As pictorially represented in FIG. 2, after peeling the protective strip 40 from template 30 to expose the adhesively coated undersides of the closure components, the surgeon positions the template with transverse line 28 in alignment with the intended incision line 70, thereby precisely to place the innermost tabs of closure components 16, 18, 20 and 22, 24, 26 substantially equidistantly from the incision line and, more importantly, at the distance "X" from one another. By virtue of the chemical mating of the adhesive coatings on the closure components and on the patient's body, the surgeon need only apply light pressure to each of the six closure components to firmly adhere them to the skin. In so doing, the surgeon easily, rapidly and accurately affixes the opposed closure components directly to the patient's skin in precise alignment on opposite sides of the incision line and at a fixed and constant distance "X" from one another.

Figure 3:
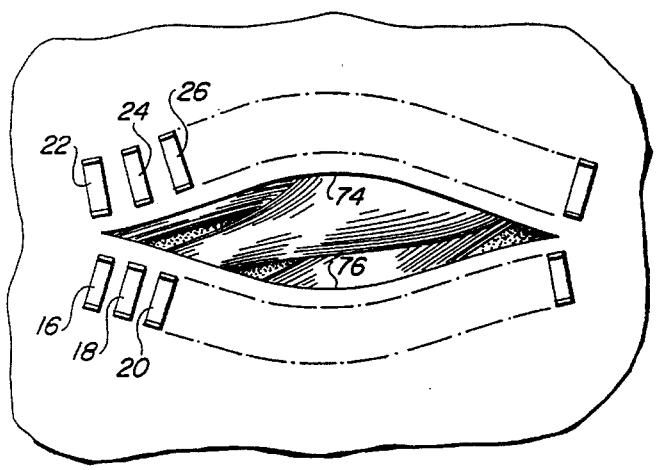
FIG. 3 is a plan view illustrating a retracted incision, and placement of the closure components relative to its edges.

This procedure is repeated until the required number of templates have been applied to the patient's skin in side-by-side proximity, following which the templates are all removed in turn, leaving behind two rows of closure components firmly adhered to the skin along opposite sides of the intended incision, each row in the described embodiment having twenty-one uniformly spaced components. The surgeon then makes the incision along the line 70 through the skin, subcutaneous tissues and muscle as necessary to expose the surgical site. Upon reaching the surgical site the surgeon can, if necessary, retract the opposed tissue layers in conventional manner as shown in FIG. 3. Since the closure components, now firmly affixed to the skin, are spaced from the edges 74 and 76 of the incision, they are not affected by, nor do they interfere with, the use of retractors or other instruments or procedures attendant the surgery.

Figure 4:
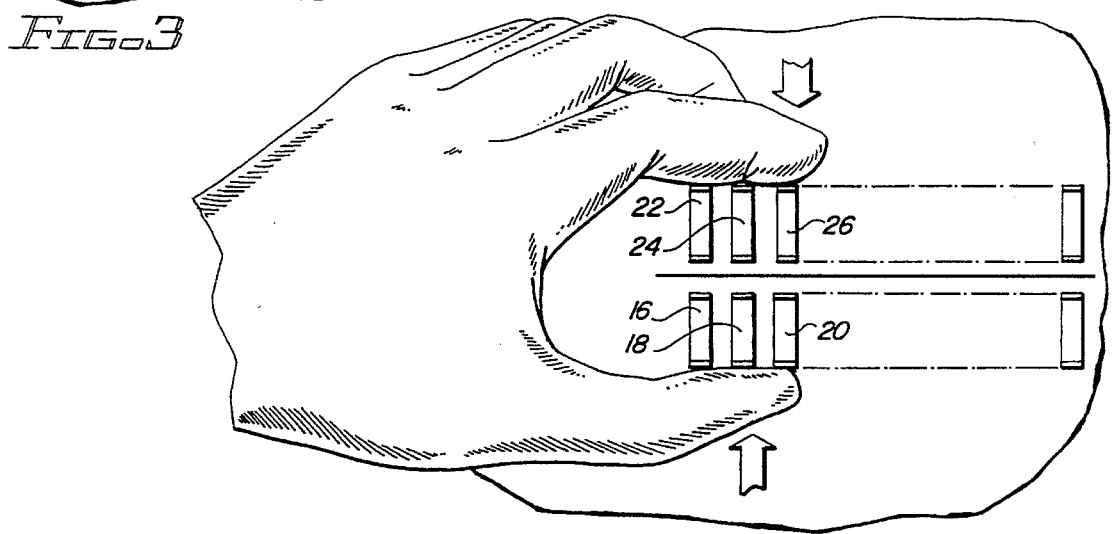
FIG. 4 is a plan view illustrating the manner in which an incision is closed by finger-pressing opposed sets of closure components toward one another.
Figure 5:
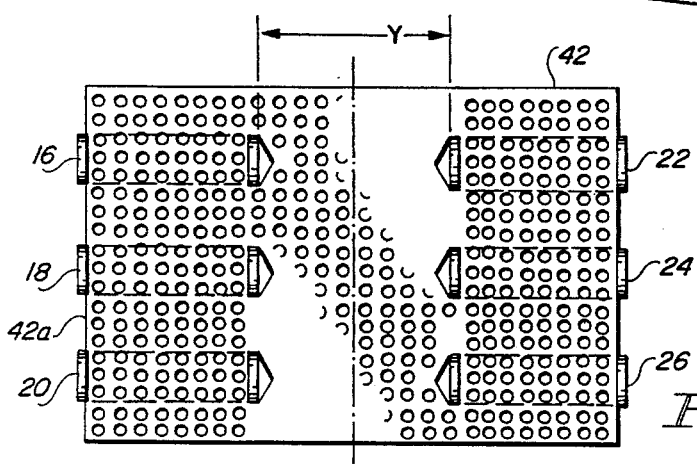
FIG. 5 is a plan view of a cover sheet in operative relationship with opposed sets of closure components.

After the surgical procedure is completed and the incision initially closed in conventional fashion by suturing the subcutaneous layers, leaving only the dermis for closing, the edges of the incision are reapproximated and, if called for, blotted dry with sterile gauze. The epidermis is then closed by bridging the incision with a multiplicity of cover sheets 14, one for each of the initially-adhered opposed sets of closure components, opposite ends of which are each anchored to three closure components of an opposed set. In practice, a nurse removes coated protective strip 60 from approximately one-half the length of the cover sheet 42 and hands it to the surgeon who, starting at one end of the incision, places the exposed tacky side over the tabs of the three enclosure components located on one side of the incision, say closure components 16, 18 and 20, with its left end 42a abutting the inner surface of the upstanding tabs furthest removed from the incision, and its slots 44, 46 and 50 receiving and engaging the innermost tabs of closure components 16, 18 and 20, respectively. After firmly pressing the left-hand half of the cover sheet down over these upstanding tabs and into contact with the patient's skin, the surgeon starts to peel the protective strip 60 from the other half of cover sheet 42 and, at the same time, finger-presses the two sets of three components toward one another, as depicted in FIG. 4, until punched slots 52, 54 and 56 engage the innermost tabs of closure components 22, 24 and 26, respectively, adhered to the skin at the other side of the incision, and then firmly presses the cover sheet down over these tabs into contact with the skin. After assuring that the edges 74 and 76 of the portion of the incision bridged by the first to be applied cover sheet are properly approximated, a cover sheet is applied in similar fashion to the next adjacent opposed sets of closure components, and so on until all closure components have been bridged. The arcuate shape of the upper ends of tabs 20b and 20c, and the triangular shape of the slots, together with the fact that the tabs are imperforate and free of adhesive, allows the slots in the cover sheet to readily slip over and frictionally engage the tabs, resulting in rapid and accurate closing of the wound.

Figure 6:
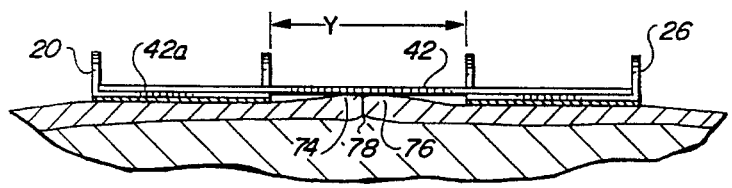
FIG. 6 is a side view of FIG. 5 illustrating "tenting" of opposite edges of a bridged incision.

Cover sheet 42 achieves the desired everting contact of the edges of the incision by reason of the fact that the span of the bridge between the innermost tabs of opposed sets of closure components is the second distance "Y" which, in the present embodiment is 17 mm, two millimeters less than the distance "X" initially established between them prior to making the incision. Thus, each transparent, inelastic and thus unstretchable, cover sheet 42 brings respective opposed sets of closure components closer together, by a predetermined precise amount, than they were initially adhered to the skin. This not only contributes to the accuracy of re-juxtaposition of the skin, but also draws the closure components toward each other sufficiently to bring the edges of the wound into everting or "tenting" contact 78, as shown in FIG. 6, under a slight, but precise amount of tension. Although cover sheet 42 is in direct contact with the skin, because it is perforated moisture from the body is allowed to escape and air to reach the wound to promote healing. The cover sheet can be punctured as may be desired to permit insertion of drains for removal of blood and other fluids from the wound during healing.

Closure of an incision several inches long can be accomplished in a few minutes, considerably less time than is required for either suturing or stapling. The entire surface area of each perforated cover sheet 42 and the bottom wall of the closure components being in contact with the skin, the "tenting" tension is maintained throughout the healing process and the buckling and puckering of stretched epidermal areas typically encountered when the incision is sutured or stapled are eliminated, along with the scars.

Seven to ten days after the operation, by which time the incision will have healed more completely than would be the case if sutures or staples were used which require removal within four or five days following surgery, the cover sheets closing the incision are swabbed with a solution which dissolves the adhesive with which the cover sheets and closure components were coated; for example, a ketonic solvent such as acetone, methyl ethyl ketone, and the like will dissolve the adhesive within minutes, allowing the cover sheets, along with the closure components, to be peeled from the surgical area.

Figure 2:
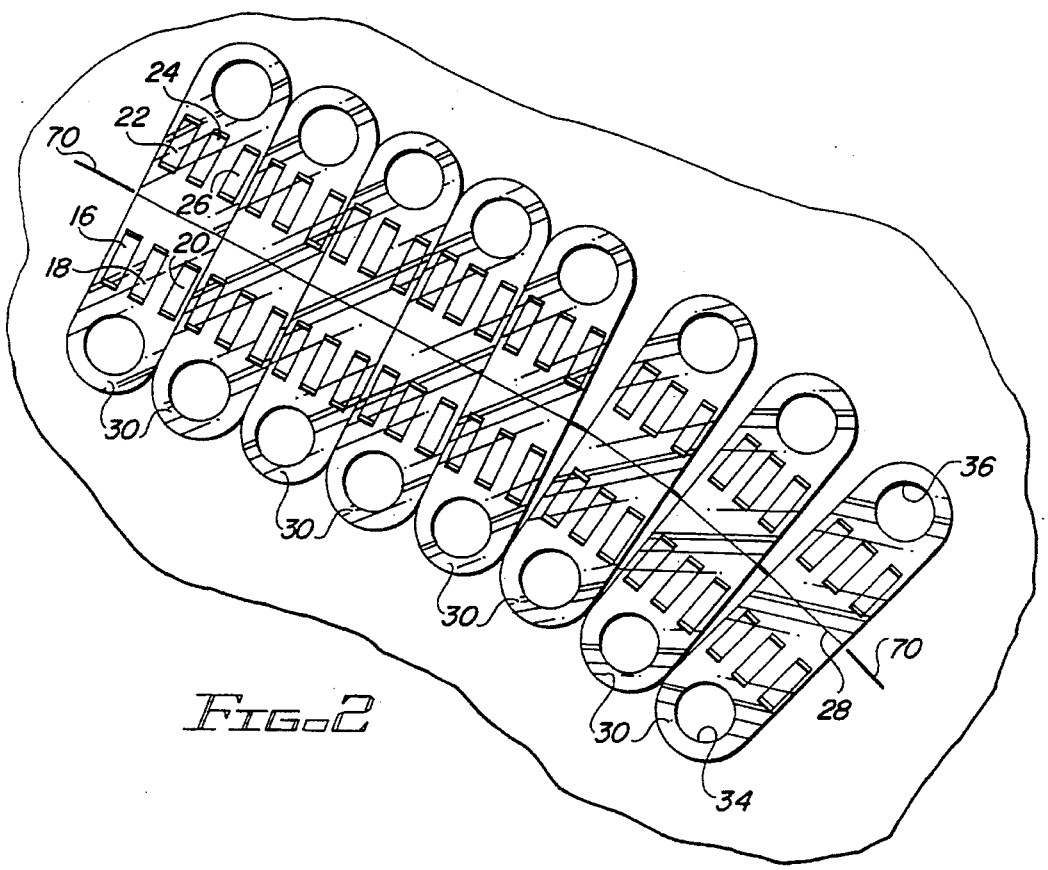
FIG. 2 is a perspective view showing a multiplicity of closure units in place on a patient's body prior to making an incision.

It will now be apparent to ones skilled in the art that various changes may be made in the invention without departing from its spirit and scope. For example, while the invention has been described as applied to a straight line incision, it is equally applicable to curved incisions, as well as to incisions made at right angles to each other and defining a flap. If the incision is curved, instead of placing templates 30 side-by-side, they can be fanned out along the incision line as depicted in FIG. 2. Such fanning of the templates, which their relatively narrow widths makes possible, positions the closure components along curved lines closely approximating the curvature of the intended incision. Also, although for most surgical situations templates one-inch wide and two-inches long are preferred for their convenience and ease of application, their size and also that of the cover sheet may be changed to accommodate either more or less closure components than the three shown, which also may have different dimensions. Moreover, the described values of the dimensions "X" and "Y" are intended to be exemplary only and may be varied within reasonable limits so long as the dimension "Y" is sufficiently less than dimension "X" that the cover sheet brings opposed edges of the incision into everting contact under slight tension.

Therefore, it is not intended that the invention be limited to the details shown and described herein but, rather, the intention is to cover all such changes and modifications as come within the spirit and scope of the appended claims.

What is claimed is:

1. A closure unit for effecting final closure of a surgical incision in a patient's body, comprising:

an elongate alignment template having length and width and having two sets of paired slits therein arrayed in precisely aligned opposing relationship and spaced a first distance from one another along the length dimension of the template, and a plurality of closure components, each frictionally engaged by a respective pair of slits in said alignment template and each comprising a thin rectangular strip of body-compatible material having an elongated bottom wall and integral upstanding tabs at opposite ends of said bottom wall, wherein the underside of said bottom wall is pre-coated with an adhesive for adhering said closure components to a patient's skin.

2. A closure unit as defined in claim 1, wherein the underside of the bottom wall of each closure component is pre-coated with a solution of natural rubber.

3. A closure unit as defined in claim 1, wherein said alignment template is fabricated from sheet polyester resin, wherein said closure components are fabricated from stainless surgical steel and each has a perforate bottom wall, and wherein the adhesive coating on said closure components is protected by a peel-away strip.

4. A closure unit as defined in claim 3, wherein said alignment template has a thickness in the range between about 10 mm and about 15 mm.

5. A closure unit as defined in claim 4, wherein the bottom wall of each closure component has a thickness of about 0.5 mm.

6. A closure unit as defined in claim 5, wherein said upstanding tabs of each closure component are imperforate.

7. A closure unit as defined in claim 3, wherein said peel-away strip is siliconized release paper.

8. A closure device as defined in claim 1, wherein each set of paired slits comprises three pairs of I-shaped slits each having a long segment and a perpendicular shorter segment at each end thereof and said long segment is disposed parallel to the width dimension of said template and to each other, and distributed across the width dimension of the template.

9. A closure unit as defined in claim 8, wherein said alignment template is fabricated from transparent polyester resin sheet, and wherein said alignment template has a transverse line thereon equidistant from opposing ends of said opposed sets of closure components adapted to be aligned with an intended incision line for positioning opposing closure components substantially equidistant from the incision line.

10. System for effecting final closure of a surgical incision made along an incision line marked on a patient's skin at the site of intended surgery, said system comprising:

an alignment template having length and width dimensions and having two sets of paired slits frictionally holding two sets of adhesively-coated closure components in aligned opposing relationship and spaced a predetermined first distance from one another along the length dimension of said template, for positioning said closure components on opposite sides of said incision line for adherence to the patient's skin, which template is adapted to be removed prior to making the incision, leaving said closure components adhesively secured to the patient's skin in said aligned opposing relationship and spaced said first distance from one another transversely of said incision line; and for closing the incision following completion of the surgery, an elongate cover sheet adapted to span said incision line and having formed therein two sets of paired slits in aligned opposing relationship arrayed each to receive and engage a respective closure component of an opposed pair and spaced from one another along a length dimension of the cover sheet a second distance sufficiently shorter than said first distance as to bring said opposed closure components closer together and draw opposed edges of the incision into alignment and everting contact under slight, but precise tension.

11. System as defined in claim 10, wherein each closure component comprises a thin elongate strip of body-compatible material having an integral upstanding tab at each end, the underside of which is coated with an adhesive, wherein the adhesively coated undersides of said closure components are protected by a peel-away strip, and wherein each slit of a pair punched in said template frictionally engages an upstanding tab of a closure component; and wherein said two opposed sets of slots in said cover sheet are arrayed in aligned opposing relationship each to receive the innermost upstanding tab of a respective closure component of an opposed pair.

12. System as defined in claim 11, wherein said alignment template is fabricated from polyester resin sheet;

wherein each closure component is formed of stainless surgical steel and has a perforate bottom wall and imperforate upstanding tabs; and wherein said cover sheet is fabricated from perforate, non-stretchable polyester resin sheet and has an adhesive coating thereon, the top and bottom surfaces of which are protected by respective peel-away strips.

13. System as defined in claim 12 wherein said alignment template has a thickness in the range between about 10 mm and about 15 mm, and wherein said closure components are formed of stainless surgical steel and have a thickness of about 0.5 mm.

14. A method for opening and closing a surgical incision, comprising the steps of:

(1) marking an incision line on the body of a surgical patient along which the intended incision is to be made;

(2) adhering to the patient's skin along opposite sides of said incision line a plurality of adhesively coated closure components precisely aligned in opposing relationship and spaced a first distance from one another transversely of the incision line by aligned paired slits punched in an alignment template and spaced from one another by said first distance, each pair of slits frictionally holding a respective closure component;

(3) prior to making an incision, removing said alignment template, leaving said plurality of closure components adhesively secured to the patient's skin;

(4) making an incision along the incision line through the patient's skin and subcutaneous tissue layers and performing the surgical procedure; and (5) closing the incision by first suturing said subcutaneous tissue layers and then bridging the space between the opposing closure components adhered to the patient's skin with a cover sheet having therein aligned paired slots arrayed each to receive and engage a respective closure component of an opposed pair and spaced from one another a second distance sufficiently shorter than said first distance as to draw opposed edges of the incision together in everting alignment under slight, but precise tension.

15. Method as defined in claim 1 wherein in step (2) said alignment template is positioned on the patient to space said opposing closure components substantially equidistantly from said incision line.

16. Method as defined in claim 14, wherein each alignment template is transparent and has printed thereon a line equidistantly spaced from said opposed pairs of slits, and wherein step (2) includes the step of aligning said printed line with said incision line for positioning said opposed closure components substantially equidistantly from said incision line.

17. Method as defined in claim 14, wherein the method comprises the further step of applying a first adhesive to the portion of the patient's body about to undergo surgery, and wherein said closure components are adhered to the patient's skin with a coating of adhesive on a surface of each closure component which contacts and mates with said first adhesive on the patient's skin.

18. Method as defined in claim 17, wherein the adhesive applied to the patient's skin is tincture of benzoine and the mating adhesive coating on said closure components is natural rubber.

19. Method as defined in claim 14, wherein said cover sheet is inelastic and perforated and coated with an adhesive which mates with a first adhesive applied to an area of the patient's skin around the incision.

20. Method as defined in claim 19, wherein said method comprises the further step, following healing of the incision, of removing said cover sheet and closure components by dissolving with a suitable solvent the adhesives adhering them to the patient's skin.

* * * * *